United States Patent [19]

Cavazza

[11] 4,415,589

[45] Nov. 15, 1983

[54] USE OF CARNITINE AND OF LOWER ACYL-CARNITINES IN THE THERAPEUTIC TREATMENT OF THE PATHOLOGY OF THE VEINS

[75] Inventor: Claudio Cavazza, Rome, Italy

[73] Assignee: Sigma-Tau Industrie Farmaceutiche Riunite S.p.A., Rome, Italy

[21] Appl. No.: 438,012

[22] Filed: Nov. 1, 1982

[30] Foreign Application Priority Data

Nov. 6, 1981 [IT] Italy .............................. 49655 A/81

[51] Int. Cl.$^3$ .................... A61K 31/22; A61K 31/205
[52] U.S. Cl. .................................................... 424/311
[58] Field of Search ................................ 424/311, 316

[56] References Cited

U.S. PATENT DOCUMENTS

| 4,255,449 | 3/1981 | Cavazza | 424/316 |
| 4,343,816 | 8/1982 | Cavazza | 424/316 |
| 4,346,107 | 8/1982 | Cavazza | 424/316 |

*Primary Examiner*—Stanley J. Friedman
*Attorney, Agent, or Firm*—Ladas & Parry

[57] ABSTRACT

Based on the discovery that carnitine and some lower acyl-carnitines act on the phospholipids in the wall of erythrocytes restoring the elasticity of the erythrocytic membrane, a new therapeutic use of the compounds mentioned above in the treatment of the pathology of the veins, typically venous stasis, is disclosed.

3 Claims, No Drawings

USE OF CARNITINE AND OF LOWER ACYL-CARNITINES IN THE THERAPEUTIC TREATMENT OF THE PATHOLOGY OF THE VEINS

The present invention relates to a new therapeutic use of carnitine and lower acyl-carnitines. More particularly, this use pertains to the treatment of peripheral vasculopathy and, even more specifically, to the treatment of pathology of the veins. The present invention also relates to orally or parenterally administrable pharmaceutical compositions for use in said treatment.

Previous uses of carnitine and of some acyl-carnitines in the treatment of peripheral vasculopathies are already known.

In the Italian patent application Serial number 49353 A/78, filed Mar. 15, 1978, in the name of the same applicant as the present application, the use of carnitine was described in the therapeutic treatment of some arterial vasculopathies whose etiologies can be traced to an altered ratio between low density lipoproteins + very low density lipoproteins and high density lipoproteins.

In the Italian patent application Serial number 47976 A/79, filed Feb. 12, 1979, in the name of the same applicant as the present application, the use of some acyl-carnitines (for example, acetyl-carnitine) was described in the therapeutic treatment of functional peripheral vasculopathies of the arteries, for example, Raynaud's disease and acrocyanosis. As known, the etiology of this last group of vasculopathies is not correlated to the previously mentioned lipoprotein ratio but seems to be dependent on an altered activity of the neurovegetative system.

In any case, a previous therapeutic use of carnitine and acyl-carnitine in the treatment of pathology of the veins has never been described.

It has now been discovered that carnitine and the lower acyl-carnitines wherein the acyl radical contains from 2 to 4 carbon atoms (acetyl-carnitine, propionyl-carnitine, butyryl-carnitine, hydroxybutyryl-carnitine and acetoacetyl-carnitine) act on the phospholipids in the erythrocyte wall restoring the elasticity of the erythrocytic membrane in cases in which this elasticity has been compromised or altered by pathological factors. Particularly effective are the levo optical isomers of the foregoing compounds: L-carnitine, acetyl L-carnitine, propionyl L-carnitine, butyryl L-carnitine, hydroxybutyryl L-carnitine and acetoacetyl L-carnitine. Also the pharmaceutically acceptable salts of the foregoing compounds (e.g. L-carnitine hydrochloride) can be used.

It has also been found that several pathological phenomena which concern the microcirculation are largerly provoked, not so much by the decreased size of the lumen of the capillaries consequent to dyslipidemic phenomena, but rather by the decreased elasticity of the erythrocytic membrane which does not permit the erythrocytes to change shape in order to adapt themselves to the shape and dimensions of the capillary lumens. Therefore, carnitine and the lower acyl-carnitines mentioned previously can be used effectively in the treatment of all those pathological states whose etiology is ascribed to decreased elasticity of the erythrocytic wall.

A non-limitative example of such a new therapeutic use of carnitine and the lower acyl-carnitines mentioned above is the treatment of venous stasis.

Carnitine and the previously mentioned acyl derivative of carnitine or the pharmacologically acceptable salts thereof are administered either via the oral route or via the parenteral route.

The dose to be administered will be determined by the attending physician taking the age, weight and general conditions of the patient into account, in accordance with an appropriate professional assessment. Although effective results may be noted at doses as low as 5–8 mg/kg of body weight per day, a dose between approximately 10 and 50 mg/kg of body weight is preferred. Should it be deemed necessary, larger doses can be administered, in view of the remarkably low toxicity of carnitine and its acyl derivatives.

In practice, carnitine and the acyl-carnitines (in the racemic form or, preferably, in the separated stereoisomer L form) are administered either orally or parenterally, in any of the usual pharmaceutical forms prepared by means of conventional processes well known to those skilled in the art. These forms comprise forms of oral unit dosages, either solids or liquids, such as lozenges, capsules, solutions, syrups and the like, and injectable forms such as sterile solutions for ampoules and vials.

Some non-limitative examples of suitable compositions for oral and parenteral administration are given below.

EXAMPLE 1

Solution or sterile aqueous solution containing carnitine or an acyl carnitine in concentrations from 50 mg to 500 mg per ml.

(a) The excipient for injectable ampoules/vials is prepared in accordance with the following non-limitative composition:

sodium carboxymethyl cellulose (low viscosity): 10 mg/kg
polysorbate 80: 4 mg/kg
propylparaben: 0.4 ml/ml
sufficient water for injections for 1-ml, 2-ml, 5-ml and 10-ml amoules/vials.

(b) The excipient for drip bottles containing 50 ml, 100 ml, 250 ml, 500 ml or 1000 ml, is prepared in accordance with the following non-limitative composition:

NaCl: 8.6 g/lt
KCl: 0.3 g/lt
$CaCl_2$: 0.33 g/lt
sufficient water for injections to produce 1 liter.

(c) The excipient for bottles for oral administration containing from 5 ml to 100 ml is prepared in accordance with the following non-limitative composition:

mannitol: 11 mg/ml
sorbitol: 600 mg/ml
sodium benzoate: 3 mg/ml
orange extract: 200 mg/ml
vitamin $B_{12}$: 3 mcg/ml
sufficient purified water.

EXAMPLE 2

Lozenges containing from 25 mg to 500 mg of carnitine or an acyl-carnitine. The excipient is prepared in accordance with the following non-limitative composition:

starch: 45%
avicel: 45%
talc: 10%

EXAMPLE 3

Capsules containing from 25 mg to 500 mg of carnitine or an acyl-carnitine without excipients.

The efficacy of the therapeutic method of the present invention has been confirmed by numerous clinical cases, some of which are hereinbelow described.

Patient 1: female—42 years—venous stasis due to valvular insufficiency of the right inner saphenous vein. Feeling of intolerable weight and evident edema. Treated with phlebotonic drugs with little success. Acetylcarnitine was administered orally at a dose of 1.6 g for 4 days and 1 g for 18 days.

Preceeding therapy was suspended. After 4 days of therapy the sensation of local weight was markedly reduced and the edema started to decrease. On the 12th day local discomfort disappeared and the edema was reduced by 50%. Simultaneously diuresis increased without the use of diuretics. On the 20th day the edema was further reduced leaving some liquid content in the malleoli.

Patient 2: female—28 years—venous stasis due to valvular insufficiency of the right external saphenous vein and bilateral varicose veins. At the 6th month of pregnancy. Feeling of weight, heavy legs and edema of the legs and feet. The patient was not under any therapy for fear of endangering pregnancy. Oral treatment with acetylcarnitine was begun at a dose of 1 g per day. Treatment was protracted for 21 days. After 8 days of therapy the subjective symptoms started to regress. The maximum effect was observed on the 14th day. The edema gradually decreased starting from the 5th day of treatment and was reduced by 90% on the 21st day. Slight increase in diuresis without diuretic treatment.

Patient 3: female—48 years—obese with light signs of cardiac insufficiency. Venous stasis due to valvular insufficiency in the left external saphenous vein and bilateral varicose veins possibly complicated by cardiac insufficiency. Heavy legs, asthenia, formication and notable edema of the foot and leg. The patient was given digitalis and diuretics to improve cardiac performance. After 12 days the edema was reduced by 20% and the signs of cardiac insufficiency (dyspnea) disappeared. Venous insufficiency, heavy legs, formication and edema continued. Diuretic treatment was suspended. A small dose of digitalis was maintained. Oral treatment with acetylcarnitine at a dose of 1 g per day was initiated. After 8 days of treatment pain and the sensation of heavy legs were notably diminished and the edema was further reduced. After another 13 days of treatment the subjective symptoms disappeared as did the edema.

Patient 4: female—second pregnancy at the 9th month. Varicose veins in the legs and malleolar edema had been present for 2 months. Feeling of heavy legs. No treatment in progress. Acetyl-carnitine was given orally at a dose of 1 g per day. After two weeks heaviness of the legs and edema disappeared.

Patient 5: male—60 years—post-phlebitic syndrome with left venous insufficiency. Small bilateral varicose veins. Feeling of weight, pain, burning; intense edema on the left. Slight malleolar edema on the right. The patient received antibiotic therapy only. Oral treatment with propionylcarnitine was begun at a dose of 1 g per day. On the 12th day there was improvement in the subjective and objective symptomatology. Subjective symptoms disappeared on the 18th day. Regression of the edema on the 28th day.

Patient 6: male—56 years—post-phlebitic syndrome with left venous insufficiency. Bilateral varicose veins. Feeling of heaviness of both legs. Pain and cramps on the left. Evident edema on the left, and slight edema on the right. Propionylcarnitine was given orally at a dose of 1 g per day. Duration of treatment 3 weeks. Subjective and objective improvement starting from the 4th day. Regression of syptoms on the 18th day.

What is claimed is:

1. A therapeutical method for the treatment of a patient affected by venous stasis which comprises orally or parenterally administering to said patient a therapeutically effective amount of carnitine, a lower acyl-carnitine wherein the acyl radical contains from 2 to 4 carbon atoms or a pharmaceutically acceptable salt thereof.

2. The method of claim 1 wherein said lower acyl-carnitine is selected from the group consisting of acetyl-carnitine, propionyl-carnitine, butyryl-carnitine, hydroxybutyrylcarnitine and acetoacetyl-carnitine.

3. The method of claim 1 wherein said carnitine and lower acyl-carnitine are the levo optical isomers thereof.

* * * * *